US008715351B1

(12) United States Patent
Pinto

(10) Patent No.: US 8,715,351 B1

(45) Date of Patent: May 6, 2014

(54) EXPANDABLE INTERBODY FUSION DEVICE WITH GRAFT CHAMBERS

(71) Applicant: Spine Wave, Inc., Shelton, CT (US)

(72) Inventor: Fabio Amaral Pinto, Stamford, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 13/689,046

(22) Filed: Nov. 29, 2012

(51) Int. Cl.
*A61F 2/44* (2006.01)

(52) U.S. Cl.
CPC ............... *A61F 2/442* (2013.01); *A61F 2/4455* (2013.01); *A61F 2/447* (2013.01)
USPC .................. 623/17.15; 623/17.11; 623/17.16; 623/17.13

(58) Field of Classification Search
CPC ........ A61F 2/461; A61F 2/442; A61F 2/4455
USPC ........... 623/17.13, 17.15, 17.16; 606/60, 246, 606/247, 249
See application file for complete search history.

(56) References Cited

U.S. PATENT DOCUMENTS

| | | | | |
|---|---|---|---|---|
| 3,486,505 | A | 12/1969 | Morrison | |
| 4,524,766 | A | 6/1985 | Petersen | |
| 4,683,476 | A | 7/1987 | Ferrari et al. | |
| 4,736,738 | A | 4/1988 | Lipovsek et al. | |
| 4,755,797 | A | 7/1988 | Kanaya | |
| 4,863,476 | A | 9/1989 | Shepperd | |
| 4,888,024 | A | 12/1989 | Powlan | |
| 5,059,193 | A | 10/1991 | Kuslich | |
| 5,192,326 | A | 3/1993 | Bao et al. | |
| 5,192,327 | A | 3/1993 | Brantigan | |
| 5,197,971 | A | 3/1993 | Bonutti | |
| 5,298,254 | A | 3/1994 | Prewett et al. | |
| 5,431,658 | A | 7/1995 | Moskovich | |
| 5,439,684 | A | 8/1995 | Prewett et al. | |
| 5,505,732 | A | 4/1996 | Michelson | |
| 5,514,180 | A | 5/1996 | Heggeness et al. | |
| 5,522,899 | A | 6/1996 | Michelson | |
| 5,571,109 | A | 11/1996 | Bertagnoli | |
| 5,591,235 | A | 1/1997 | Kuslich | |
| 5,609,636 | A * | 3/1997 | Kohrs et al. | 623/17.16 |

(Continued)

FOREIGN PATENT DOCUMENTS

| | | | |
|---|---|---|---|
| EP | 0621020 | A1 | 10/1994 |
| FR | 2639823 | A1 | 6/1990 |
| FR | 2719763 | A1 | 11/1995 |
| WO | 9902214 | A1 | 1/1999 |

OTHER PUBLICATIONS

PCT Search Report for corresponding PCT Application No. PCT/US2008/064534.

(Continued)

*Primary Examiner* — Kevin T Truong
*Assistant Examiner* — Samuel Hanna
(74) *Attorney, Agent, or Firm* — Hoffmann & Baron, LLP

(57) ABSTRACT

An expandable interbody fusion device includes superior and inferior plates that are configured to receive a sequentially inserted stack of expansion members or wafers in interlocking engagement. The superior and inferior plates have openings therethrough in communication with aligned holes through the wafers for receipt and containment of bone graft to promote fusion between opposing vertebral bodies. One of said superior and inferior endplates has a multi-contoured opening extending therethrough.

15 Claims, 8 Drawing Sheets

(56) References Cited

U.S. PATENT DOCUMENTS

| | | | | |
|---|---|---|---|---|
| 5,645,599 | A | 7/1997 | Samani | |
| 5,702,454 | A | 12/1997 | Baumgartner | |
| 5,755,797 | A | 5/1998 | Baumgartner | |
| 5,756,127 | A | 5/1998 | Grisoni et al. | |
| 5,766,252 | A | 6/1998 | Henry et al. | |
| 5,836,948 | A | 11/1998 | Zucherman et al. | |
| 5,860,977 | A | 1/1999 | Zucherman et al. | |
| 5,891,147 | A | 4/1999 | Moskovitz et al. | |
| 5,951,553 | A | 9/1999 | Betz et al. | |
| 5,980,522 | A | 11/1999 | Koros et al. | |
| 6,033,411 | A | 3/2000 | Preissman | |
| 6,045,579 | A | 4/2000 | Hochshuler et al. | |
| 6,066,154 | A | 5/2000 | Reiley et al. | |
| 6,074,390 | A | 6/2000 | Zucherman et al. | |
| 6,110,179 | A | 8/2000 | Flivik et al. | |
| 6,110,210 | A | 8/2000 | Norton et al. | |
| 6,159,211 | A | 12/2000 | Boriani et al. | |
| 6,159,244 | A | 12/2000 | Suddaby | |
| 6,190,414 | B1 | 2/2001 | Young et al. | |
| 6,200,347 | B1 | 3/2001 | Anderson et al. | |
| 6,241,771 | B1 | 6/2001 | Gresser et al. | |
| 6,273,916 | B1 | 8/2001 | Murphy | |
| 6,279,916 | B1 | 8/2001 | Stecher | |
| 6,287,308 | B1 | 9/2001 | Betz et al. | |
| 6,287,309 | B1 | 9/2001 | Baccelli et al. | |
| 6,290,724 | B1 | 9/2001 | Marino | |
| 6,387,130 | B1 | 5/2002 | Stone et al. | |
| 6,395,034 | B1 | 5/2002 | Suddaby | |
| 6,402,750 | B1 | 6/2002 | Atkinson et al. | |
| 6,419,705 | B1 | 7/2002 | Erickson | |
| 6,432,107 | B1 | 8/2002 | Ferree | |
| 6,436,142 | B1 | 8/2002 | Paes et al. | |
| 6,478,800 | B1 | 11/2002 | Fraser et al. | |
| 6,488,710 | B2 | 12/2002 | Besselink | |
| 6,500,205 | B1 | 12/2002 | Michelson | |
| 6,520,993 | B2 | 2/2003 | James et al. | |
| 6,562,074 | B2 | 5/2003 | Gerbec et al. | |
| 6,595,998 | B2 | 7/2003 | Johnson et al. | |
| 6,620,196 | B1 | 9/2003 | Trieu | |
| 6,648,917 | B2 | 11/2003 | Gerbec et al. | |
| 6,656,178 | B1 | 12/2003 | Veldhuizen et al. | |
| 6,666,888 | B1 * | 12/2003 | Jackson | 623/17.11 |
| 6,726,691 | B2 | 4/2004 | Osorio et al. | |
| 6,740,093 | B2 | 5/2004 | Hochschuler et al. | |
| 6,837,904 | B2 | 1/2005 | Ralph et al. | |
| 6,852,095 | B1 | 2/2005 | Ray | |
| 6,852,126 | B2 | 2/2005 | Ahlgren | |
| 6,852,129 | B2 | 2/2005 | Gerbec et al. | |
| 6,863,673 | B2 | 3/2005 | Gerbec et al. | |
| 6,908,485 | B2 * | 6/2005 | Crozet et al. | 623/17.16 |
| 6,997,929 | B2 | 2/2006 | Manzi et al. | |
| 7,044,972 | B2 | 5/2006 | Mathys, Jr. et al. | |
| 7,094,257 | B2 | 8/2006 | Mujwid et al. | |
| 7,118,580 | B1 | 10/2006 | Beyersdorff et al. | |
| 7,591,852 | B2 | 9/2009 | Prosser | |
| 7,931,688 | B2 | 4/2011 | Landry et al. | |
| 7,967,867 | B2 | 6/2011 | Barreiro et al. | |
| 8,182,537 | B2 * | 5/2012 | Refai et al. | 623/17.16 |
| 8,308,805 | B2 | 11/2012 | Lynn et al. | |
| 2002/0026195 | A1 | 2/2002 | Layne et al. | |
| 2002/0147497 | A1 | 10/2002 | Belef et al. | |
| 2002/0177897 | A1 | 11/2002 | Michelson | |
| 2003/0171812 | A1 | 9/2003 | Grunberg et al. | |
| 2004/0019354 | A1 | 1/2004 | Johnson et al. | |
| 2004/0064144 | A1 | 4/2004 | Johnson et al. | |
| 2004/0220580 | A1 | 11/2004 | Johnson et al. | |
| 2005/0027364 | A1 | 2/2005 | Kim et al. | |
| 2005/0149194 | A1 | 7/2005 | Ahlgren | |
| 2006/0058807 | A1 | 3/2006 | Landry et al. | |
| 2006/0058880 | A1 | 3/2006 | Wysocki et al. | |
| 2006/0129244 | A1 | 6/2006 | Ensign | |
| 2008/0161924 | A1 * | 7/2008 | Viker | 623/17.15 |
| 2008/0172127 | A1 | 7/2008 | Perez-Cruet et al. | |
| 2008/0300598 | A1 * | 12/2008 | Barreiro et al. | 606/63 |
| 2009/0118836 | A1 * | 5/2009 | Cordaro | 623/17.16 |
| 2009/0198339 | A1 | 8/2009 | Kleiner et al. | |
| 2009/0222100 | A1 * | 9/2009 | Cipoletti et al. | 623/17.16 |
| 2010/0179656 | A1 | 7/2010 | Theofilos | |
| 2010/0286779 | A1 * | 11/2010 | Thibodeau | 623/17.11 |
| 2010/0292796 | A1 | 11/2010 | Greenhalgh et al. | |
| 2011/0130835 | A1 | 6/2011 | Ashley et al. | |
| 2012/0158144 | A1 | 6/2012 | Ullrich, Jr. et al. | |

OTHER PUBLICATIONS

Baddeley, S. and Cullen, J.C., "The Use of Methylmethacrylate in the Treatment of Giant Cell Tumours of the Proximal Tibia", Aust. N.Z. J. Surg. vol. 49—No. 1, Feb. 1979, 3 pp.

Campanacci, M., Gui, L, Ranieri, L., Savini, R., "Treatment of Tibial Plateau Fractures", Chi. Org. Mov. 72(3), Dec. 1975 (Italian text), pp. 234-256, English Translation, 15 pp.

Kyphon Inc., Surgical Technique Manual Nov. 16, 1999, pp. 5, 6, 9, 16-19.

Kyphon Vertebral Treatment Notebook, date unknown, 9 pp.

Kyphon web page, www.kyphon.com, Mar. 13, 2001, 1 p.

AOM Technique Manual, "Controlled Delivery for Osteoplasty, A Vertebroplasty Application", Cat #900.001—Rev B—date unknown.

Medtronic Sofamor Danek, "Verte-stack™, Peek Stackable Corpectomy Device, Surgical Technique", date unknown, 8 pp.

Signus Medical, Tetris, Sep. 2003, 1 p.

Blackstone Medical Inc., Construx™ PEEK VBR System, 2005, www.blackstonemedical.com, 1 p.

Globus Medical, Sustain™ R Small, date unknown, 6 pp.

* cited by examiner

EXPANDABLE INTERBODY FUSION DEVICE WITH GRAFT CHAMBERS

FIELD OF THE INVENTION

The subject invention relates generally to the field of spinal implants and more particularly to expandable interbody fusion devices with graft chambers.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

Certain spinal devices for achieving fusion are also expandable so as to correct disc height between the adjacent vertebrae. Examples of expandable interbody fusion devices are described in U.S. Pat. No. 6,595,998 entitled "Tissue Distraction Device", which issued on Jul. 22, 2003 (the '998 patent), U.S. Pat. No. 7,931,688 entitled "Expandable Interbody Fusion Device", which issued on Apr. 26, 2011 (the '688 patent), and U.S. Pat. No. 7,967,867 entitled "Expandable Interbody Fusion Device", which issued on Jun. 28, 2011 (the '867 patent). The '998 patent, the '688 patent and the '867 patent each discloses sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '998 patent, the '688 patent and the '867 patent are assigned to the same assignee as the present invention, the disclosures of these patents being incorporated herein by reference in their entirety.

Certain interbody fusion devices also include hollow portions or chambers that are filled with suitable material such as bone graft to promote fusion between vertebral bodies. The extent and size of the chambers establish areas of contact that are configured so as to assure maximum contact between the bone graft and the vertebral bodies. Sufficient surface area of the device surrounding the chambers needs to be maintained in order to provide an appropriate load bearing surface to withstand the compressive forces exerted by the opposing vertebral bodies. In addition, where expandable interbody fusion devices are used to correct height within the intradiscal space, the effect of shear forces on the expanded device due to torsional movement of the spine also needs to be considered.

Accordingly, there is a need to develop expandable interbody fusion devices with bone graft chambers that take into account and balance these factors.

SUMMARY OF THE INVENTION

It is an object of the invention to provide an improved expandable device with openings serving as bone graft chambers for implantation into the intradiscal space between two opposing vertebral bodies of a spine.

DESCRIPTION OF THE EMBODIMENTS

Figure 1:
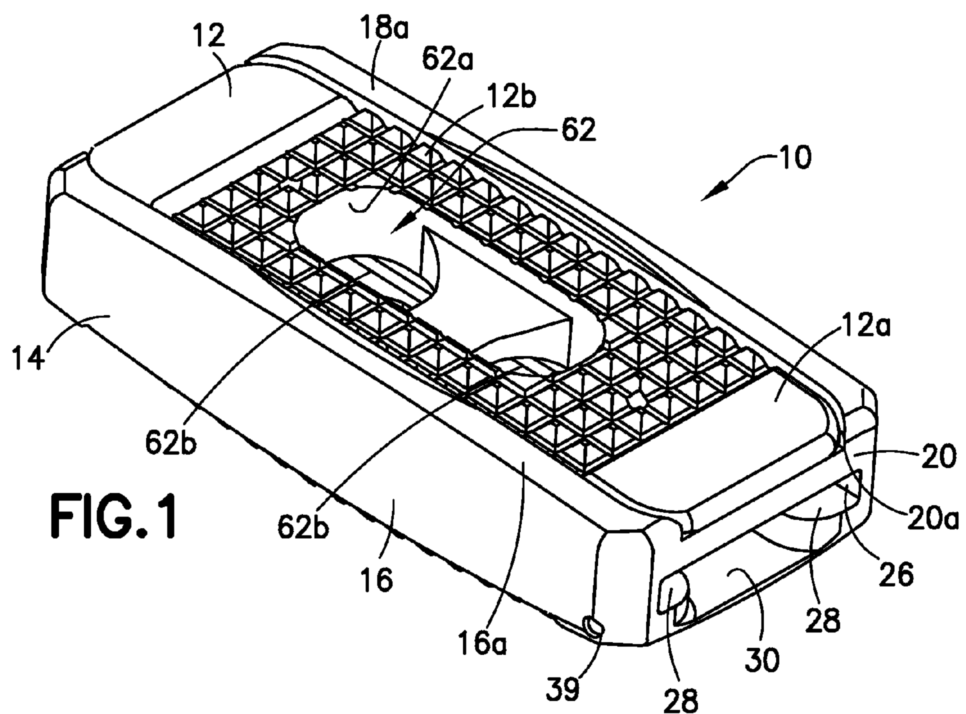
FIGS. 1 and 2 are rear and front perspective views respectively of an expandable interbody fusion device in unexpanded condition in accordance with one embodiment of the present invention.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
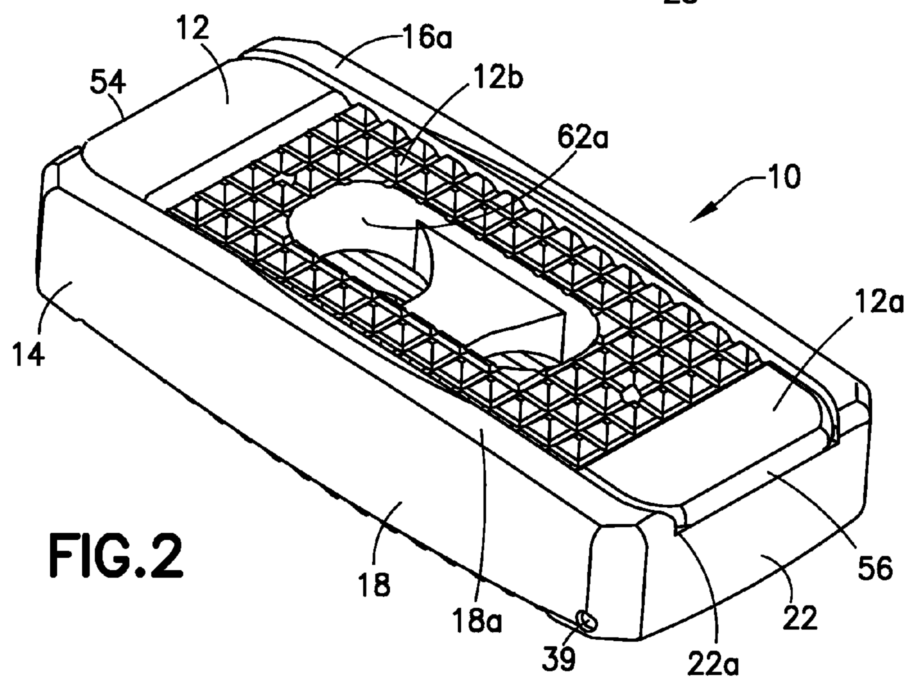
Figure 3:
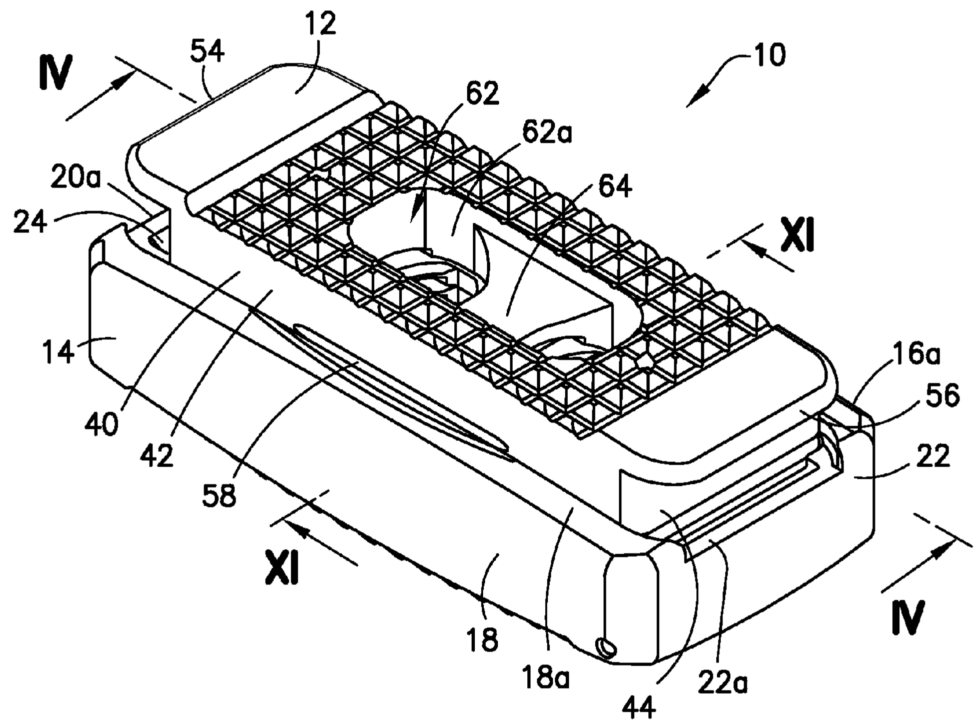
FIG. 3 is a front perspective view of the expandable interbody fusion device of FIG. 2 in expanded condition.
Figure 5:
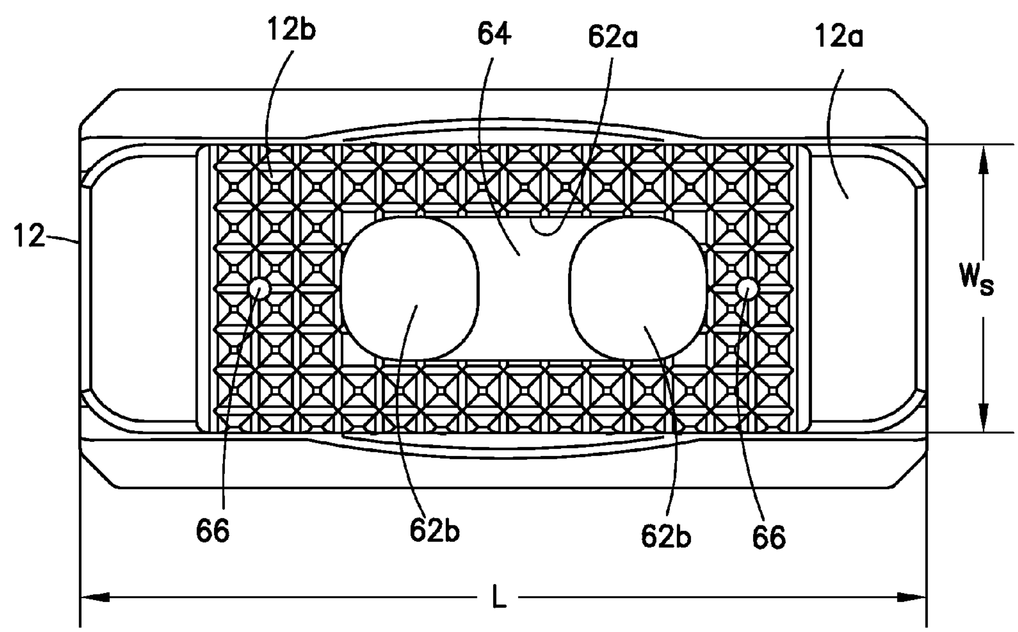
FIG. 5 is a top plan view of the interbody fusion device of FIG. 1.
Figure 6:
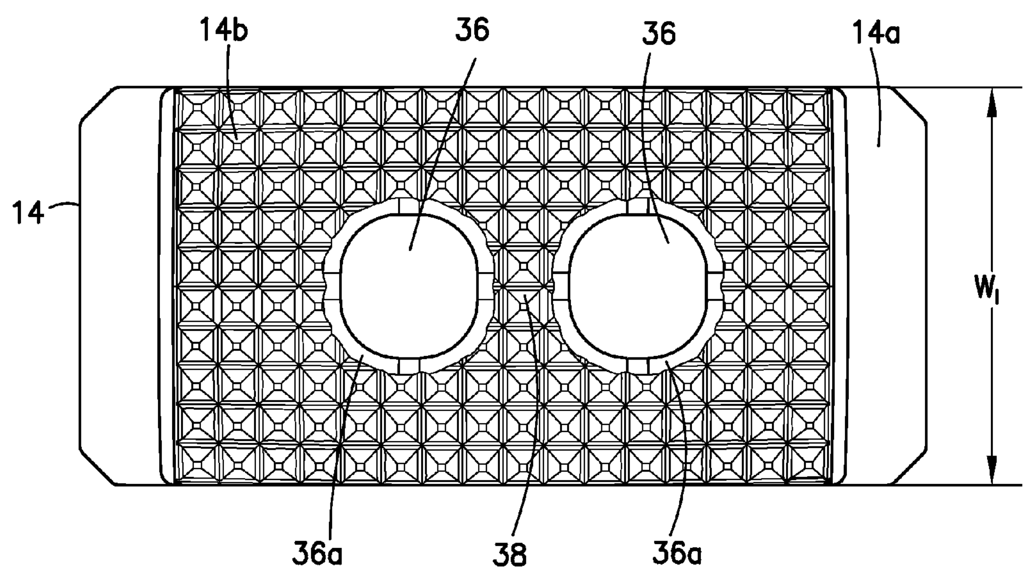
FIG. 6 is a bottom plan view of the interbody fusion device of FIG. 1.

In accordance with one embodiment of the invention, an expandable interbody fusion device 10 includes a first superior endplate 12 and a second inferior endplate 14, as shown in FIGS. 1-3. The superior outer surface 12*a* and the inferior outer surface 14*a* of the endplates 12 and 14 each define engagement ribs 12*b* and 14*b* that are configured to engage or grip the vertebral endplates of opposed vertebral bodies in a spine. Preferably, the ribs 12*b* and 14*b*, as shown also in FIGS. 5-6 are configured to prevent expulsion of the device 10 under normal spinal loads. For instance, the ribs as shown may have a pyramidal configuration or they may include a saw tooth shape that is inclined toward the opening through which the device is inserted into the intradiscal space between opposing vertebral bodies.

The interbody fusion device 10 has a height across the superior and inferior endplates 12, 14 in the unexpanded condition that is less than the normal anatomic height of a typical intradiscal space. The invention contemplates that a series of expansion members, such as interlocking wafers 100 as will be described, are introduced into the device 10 to distract the opposing vertebrae by separating the superior and inferior endplates 12, 14 in situ. Insertion of the wafers 100 separates the endplates 12, 14 to expand the height of the device within the intradiscal space and to ultimately restore the normal anatomic height of the disc space. Expansion devices of this type are shown and described in the '998 patent, the '688 patent and the '867 patent described hereinabove and incorporated herein by reference.

The present invention contemplates an improved interbody fusion device 10 that particularly includes openings and holes that define graft chambers for containment of materials that promote bone fusion through the device between opposing vertebral bodies. The inferior endplate 14 of the interbody fusion device 10 as shown in FIGS. 1-3 is elongate and comprises a pair of oppositely spaced apart sidewalls 16 and 18 extending along the longitudinal direction and projecting upwardly from outer surface 14*a*. A pair of spaced apart end walls 20 and 22 extend laterally across the device and project upwardly from the outer surface 14*a*. End wall 20 is disposed at the rear or proximal end of the device 10 and end wall 22 is disposed at the front or distal end of the device 10. The side walls 16, 18 together with rear end wall 20 and front end wall 22 form an open, upwardly facing full bounded cavity 24 as shown in FIGS. 3 and 4.

Figure 4:
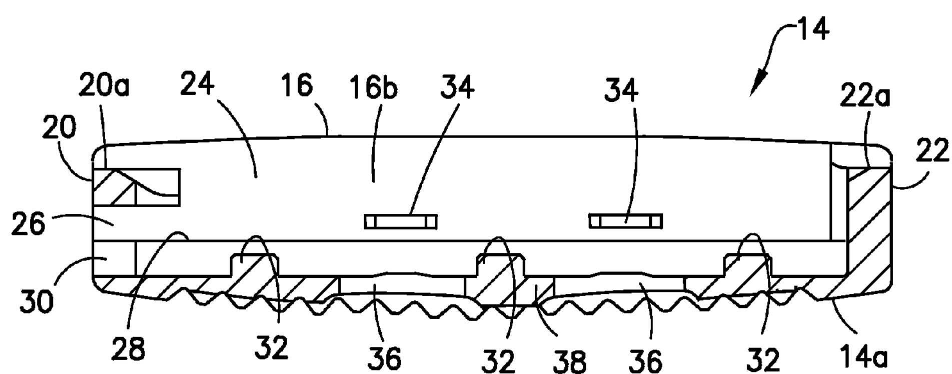
FIG. 4 is a cross section of the inferior endplate of the interbody fusion device as seen along the viewing lines IV-IV of FIG. 3.

The inferior plate 14 as shown in FIGS. 1 and 4 defines a wafer channel 26 through the rear end wall 20 and through which the wafers 100 which serve as expansion members are introduced. The inferior endplate 14 includes a pair of opposite ledges 28 that define an upper support surface on which each wafer 100 is supported as it introduced into the wafer channel 26, as will be described. The inferior endplate 14 also defines an inserter channel 30 that is below and in communication with the wafer channel 26. The ledges 28 define the bottom surface of the cavity 24. The inserter channel 30 receives a wafer track (not shown) for introduction of the wafers 100 as described in the '688 patent incorporated herein by reference. More specifically the inserter channel 30 includes a number of severable posts 32 projecting upward therein that are configured to engage an insertion plate and a release plate in a manner as described in the '688 patent.

By continued reference to FIGS. 3-4, it can be seen that each opposite side wall 16, 18 of the inferior endplate 14 has on an interior surface 16*b* thereof a pair of ribs 34 projecting into the cavity 24, the ribs 34 being spaced lengthwise on the interior of each side wall 16, 18. Each side wall 16, 18 further defines upper surfaces 16*a* and 18*a* extending lengthwise thereon and generally parallel to each other. Rear end wall 20 defines a recess 20*a* extending therein at that the upper surface thereof and front end wall 22 defines a recess 22*a* extending therein at the upper surface thereof.

As shown particularly in FIGS. 4 and 6, the inferior endplate 14 includes graft chambers defined by a pair of spaced openings 36 extending in alignment along the longitudinal direction. The openings 36 extend through the outer surface 14*a* of the inferior endplate 14, through the support surfaces defined by ledges 28 and communicate with the cavity 24. A web 38 extends between the pair of openings 36, the web 38 supporting one of the posts 32 that is used to engage an insertion plate and a release plate as indicated hereinabove. One other post 32 is disposed between a first opening 36 and the rear end wall 20 and a further post 32 is disposed between the second opening 36 and the front end wall 22, the three posts 32 and two openings 36 extending linearly along the longitudinal direction of the inferior endplate 14. Each opening 36 includes therearound a countersink surface 36*a* as shown in FIG. 6 for receipt of bone graft to thereby increase the surface area of contact between such bone graft and the endplate of a vertebral body. At least one radiopaque marker 39 may be included on the inferior endplate 14, such as adjacent the proximal end of side wall 16 and distal end of sidewall 18, as shown in FIGS. 1-2 to assist in the visualization of the insertion of device 10 into the intradiscal space.

Figure 10:
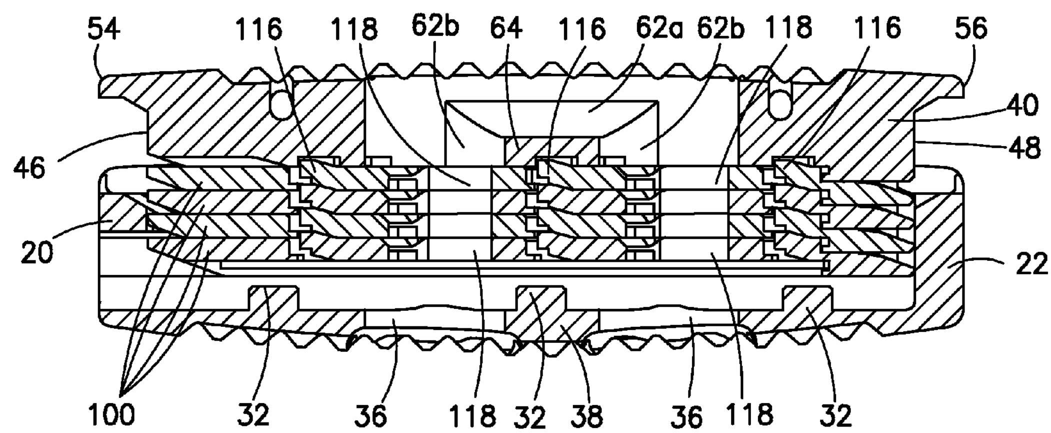
FIG. 10 is a cross section of the expanded interbody fusion device as seen along the viewing lines IV-IV of FIG. 3.
Figure 11:
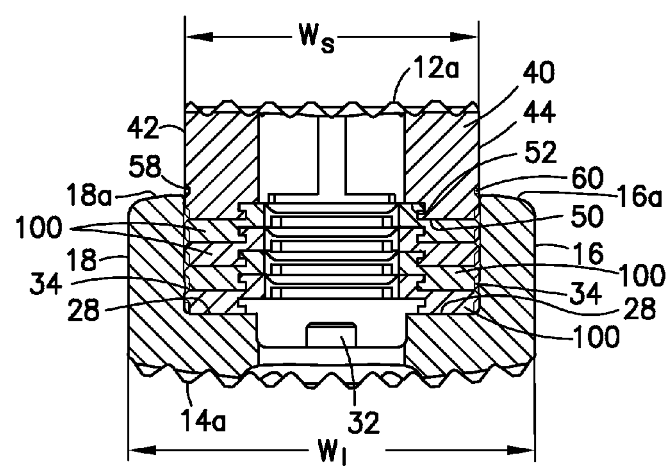
FIG. 11 is a cross section of the expanded interbody fusion device as seen along the viewing lines XI-XI of FIG. 3.

The superior endplate 12 as shown in FIGS. 1-3 and 10-11 is elongate and comprises a hub 40 having pair of side surfaces 42 and 44 extending longitudinally on each side of the hub 40 and a pair of end surfaces 46 and 48 extending respectively at the proximal end and the distal end of the superior endplate 12. The hub 40 is sized and configured to fit within the cavity 24 in relatively close fit between the side walls 16 and 18 and the end walls 20 and 22 of the inferior endplate 14. The lower surface 50 of the hub 40 (FIG. 11) includes a shaped configuration defined by wafer mating features 52 that are substantially identical to the mating features on the lower surface of each wafer 100, as will be described. Superior endplate 12 includes a flange 54 projecting outwardly and longitudinally from the hub 40 at the rear proximal end surface 46 and a flange 56 projecting outwardly and longitudinally from the hub 40 at the front distal end surface 48. The hub 40 defines a groove 58 and 60 as shown in FIGS. 3 and 11 extending along each side 42 and 44 thereof that is configured to engage the ribs 34 of the inferior endplate 14. This engagement temporarily holds the superior and inferior endplates together as the device 10 is introduced into the intradiscal space to be distracted.

As shown particularly in FIGS. 1-3 and 5, the superior endplate 12 includes a graft chamber defined by a multi-contoured opening 62 extending through the upper surface 12*a* and the lower surface 50. The opening 62 is considered multi-contoured since it has one configuration opening at the upper surface 12*a* and a different configuration opening at the lower surface 50. In this particular arrangement, upper portion of opening 62 is a single, oval-shaped opening 62*a*. The lower portion of opening 62 comprises a pair of generally circular openings 62*b* separated by a cross member 64 disposed generally centrally and transversely across superior endplate 12 in the lateral direction. Openings 62*b* extend generally linearly along the longitudinal direction of superior endplate 12 and are disposed therethrough such that in assembly with inferior endplate 14 openings 62*b* are generally in alignment in the elongate direction with openings 36 through inferior endplate 14. While the provision of cross member 64 may tend to reduce the area through which the bone graft may flow upon injection into the device 10, it should be appreciated that the cross member 64 at the lower portion of superior endplate 12 provides strength to the superior endplate 12 while allowing greater bone graft area at the outer surface 12*a*. In addition, cross member 64 allows for a locking location for the uppermost wafer 100, as will be described. It should also be appreciated that other multi-contoured shapes of openings may be used as alternatives to the illustrated and described multi-contoured opening 62. Radiopaque markers 66 may be included on the outer surface 12*a* of superior endplate 12 as shown, for example in FIG. 5.

Figure 7:
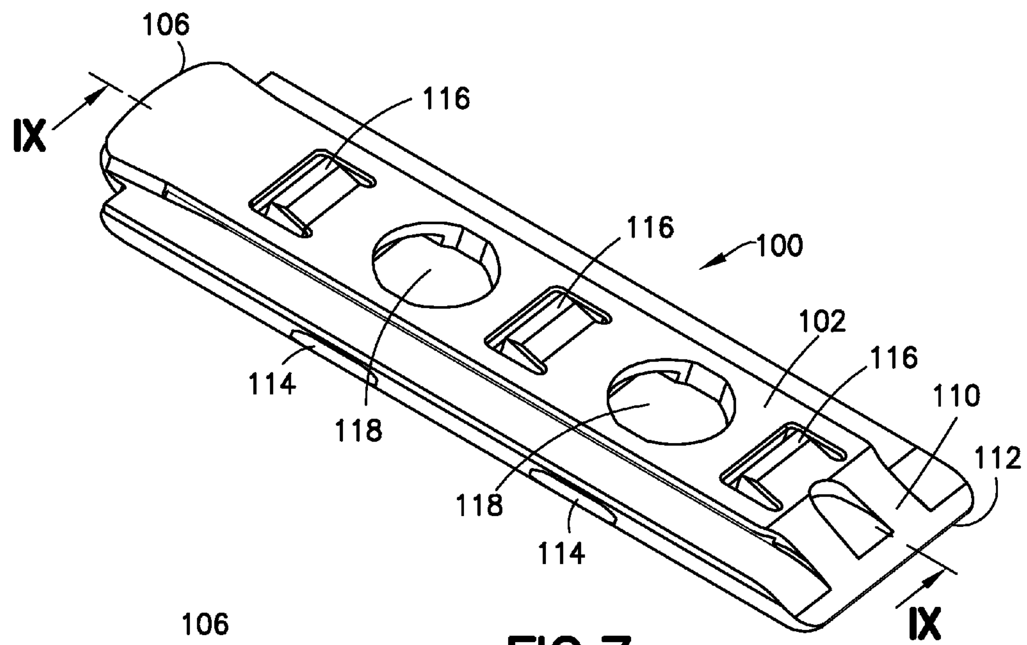
FIG. 7 is a top perspective view of an interlocking wafer serving as an expansion member to expand the interbody fusion device to the expanded condition shown in FIG. 3.
Figure 8:
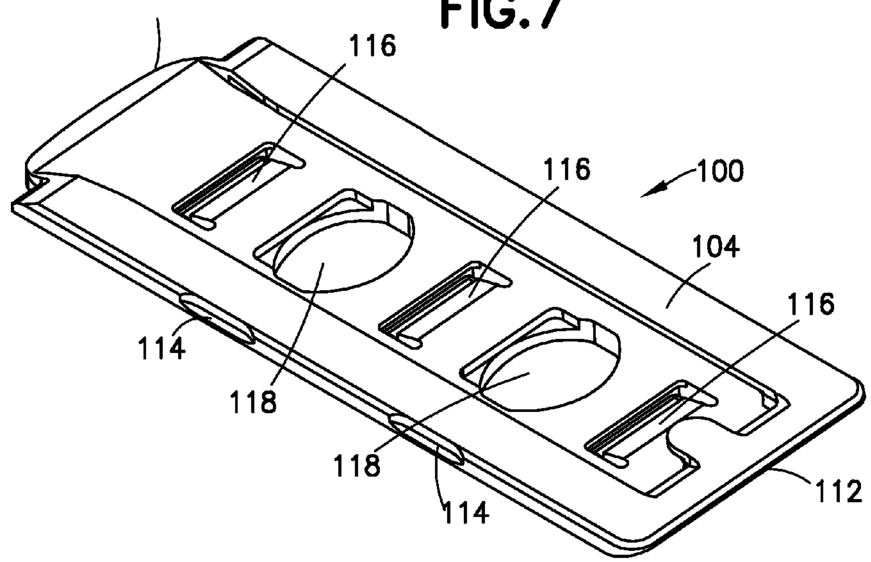
FIG. 8 is a bottom perspective view of the interlocking wafer shown in FIG. 7.
Figure 9:
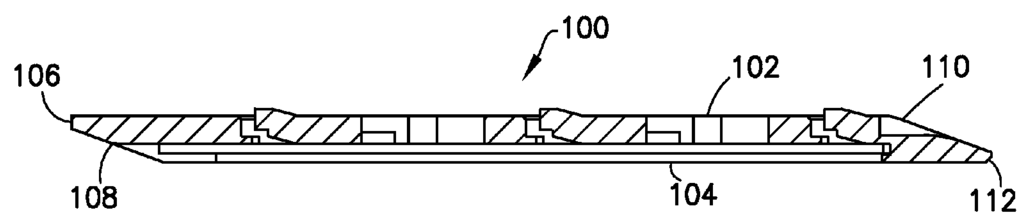
FIG. 9 is cross section of the interlocking wafer of FIG. 7 as seen along viewing lines IX-IX of FIG. 7.

Details of an interlocking wafer 100 are shown in FIGS. 7-9. The wafer 100 is elongate and has an upper surface 102 and a lower surface 104, both of which are generally planar so that the wafers can form a stable stack within the interbody fusion device 10. The trailing proximal end 106 includes a downward-facing sloped surface 108 that corresponds angularly to an upward-facing surface 110 on the leading distal end 112 of the wafer 100. The two sloped surfaces help displace an earlier inserted wafer 100 upon introduction of a new wafer. More specifically, when a first wafer is within the wafer channel 26, resting on the ledges 28 (FIG. 11), the downward-facing sloped surface 108 thereof is lifted upon contact with the upward-facing slope 110 of a newly inserted wafer. This allows the newly inserted wafer to ride along the ledges 28 until it is positioned fully underneath the previous wafer. The wafer 100 further includes notches or indentations 114 that are configured to receive the ribs 34 on the inner side walls 16, 18 of the inferior plate 14 (see FIG. 11) in a manner similar to the grooves 58 and 60 in the hub 40 of the superior endplate 12.

The wafer 100 includes several features for interlocking engagement to the hub 40 and to adjacent wafers 100 in a complementary interlocking mating interface. One particular feature includes a series of locking elements defined by resiliently deflectable prongs 116 that project outwardly above the upper surface 102 of the wafer. In one arrangement, the prongs 116 are disposed along the wafer 100, extending lengthwise in alignment and defining a plurality of resiliently deflectable locking surfaces therealong. The lower surface 104 of each wafer 100 as shown in FIGS. 8 and 11 also defines a T-slot configuration for mating with a T-bar configuration on the upper surface 102 of a successive wafer 100. It should be appreciated that the respective T-bar and T-slot configurations may be formed on either the upper surface or the lower surface of a wafer 100 as desired. The structure and function of a wafer 100 and the prongs 116 are more fully described in the '867 patent, incorporated herein by reference. In the illustrated arrangement, there are three prongs 116 extending generally linearly along the elongate longitudinal direction. A pair of holes 118 extends through the upper surface 102 and the lower surface 104 of each wafer 100. The holes 118 are provided to allow bone graft to flow through the wafers, the holes 118 being disposed along the longitudinal direction with at least one hole 118 being situated between each pair of prongs 116. Of course, it is contemplated that fewer or greater numbers of prongs 116 and holes 118 may be provided in a wafer 100 within the scope of the present invention. For instance, the number of prongs 116 and holes 118 may be adjusted based on the length of the wafer 100.

The superior and inferior endplates 12 and 14 are configured to be initially releasably engaged when the device 10 is unexpanded, as shown in FIGS. 1 and 2. In this unexpanded condition, the device 10 is attached to a track assembly as described in the '867 patent. In this stage, the hub 40 is disposed within the cavity 24 of inferior endplate 14 with the ribs 34 on the interior surfaces of side walls 16, 18 engaging the grooves 58 and 60 extending along each side of the hub 40. The lower surface 50 of hub 40 is on or closely adjacent to the wafer support ledges 28 in facing relationship. This engagement temporarily holds the superior and inferior endplates together as the device 10 is introduced into the intradiscal space to be distracted. In this unexpanded condition the outer surface 12*a* of the superior endplate 12 is substantially flush with the upper surfaces 16*a* and 18*a* of the sidewalls 16 and 18, with the flanges 54 and 56 residing in recesses 20*a* and 22*a* of the rear end wall 20 and the front end wall 22 of the inferior endplate 14, as illustrated in FIGS. 1 and 2. Such nesting of the superior endplate 12 within inferior endplate 14 allows for lower height of the unexpanded device 10.

The manner in which the interbody fusion device 10 is expanded is illustrated in FIGS. 10-11. When the first wafer 100 is introduced, the interlocking features on the upper surface 102 of the wafer 100 engage the mating features 52 on the lower surface 50 of superior endplate 12 lifting the superior endplate 12 upwardly within the cavity 24 between sidewalls 16, 18 and breaking the initial releasable engagement. When the first inserted wafer 100 is introduced into the device 10 the holes 118 in the wafer 100 are located to be in alignment and communication with the openings 62*b* extending through the lower surface 50 of inferior endplate 12. The locking elements 116 lockingly engage the lower surface 50, one adjacent each of the distal and proximal ends of superior endplate 12 and the generally central locking element lockingly engaging the lower surface of cross member 64 extending between the openings 62*b*. This process continues with each successive wafer 100 inserted beneath a previously inserted wafer 100 until a complete stack is formed, as depicted in FIGS. 10-11. As each subsequent wafer 100 is introduced, the locking elements 116 lockingly engage the mating features on the lower surfaces of each previously introduced wafer 100, with the holes 118 of each wafer 100 being inserted such that they are in alignment and communication with the holes 118 of each previously introduced wafer 100. The lowermost wafer 100 is supported on the support surfaces of ledges 28 with the holes 118 therethrough being in alignment and communication with the openings 36 extending through inferior endplate 14. It should be noted that preferably all the wafers 100, but at least the two lowermost wafers 100, are contained within and constricted by the opposing side walls 16, 18 and the rear and front end walls 20, 22 so as to provide additional resistance against torsional movement of the spine. The manner in which the expanded interbody fusion device 10 is released from the wafer track assembly of the insertion instrument by the severing of posts 32 is fully described in the '867 patent.

Having described the interbody fusion device 10, a suitable bone filler or bone graft to promote fusion between opposing vertebral bodies may be inserted into the expanded device 10 as well as into the intradiscal space adjacent to device 10. With the instrument used to insert device 10 having been removed from the expanded device 10, it can be appreciated that the wafer insertion channel 30 provides access into the expanded device 10. A suitable graft insertion instrument may be used to inject bone graft under pressure into the expanded device 10. Under an appropriate pressure, such bone graft will flow through the holes 118 extending through the wafers 100 and into the openings 36 through the inferior endplate 14 and into the multi-contoured opening 62 through the superior endplate 12. The bone graft will also flow into the countersink surfaces 36*a* surrounding the openings 36 so as to further increase contact area between the bone graft and the endplate of the inferior vertebral body. Injection of the bone graft will continue until the graft is stress loaded against the endplates of the opposing vertebral bodies. In some instances, bone graft may be pre-loaded into an unexpanded device 10 prior to insertion of the device 10 into the intradiscal disc space. Suitable bone graft materials may include autograph bone, allograft bone, bone morphogenic protein (BMP) and xenograft and synthetic derived bone substitutes, as described for example, in the '998 patent. It should also be understood that a material with a bone fusion promoting substance, such as a sponge saturated with BMP, may be placed in the single opening 62*a* of the multi-contoured opening 62 and supported by the cross member 64. This will allow the fusion promoting substance to be pre-loaded into device 10 and not be disrupted upon expansion of device 10 by insertion of wafers 100 as described herein.

It is contemplated that each of the components of the device 10, namely the superior endplate 12, inferior endplate 14 and the wafers 100 described herein, be formed of a biocompatible material that is sufficiently rigid to form a solid stack as the successive wafers are inserted into the device. Thus, in one specific embodiment, the components are formed of PEEK or a carbon-fiber reinforced PEEK, or similar polymeric material. Alternatively, the superior and inferior plates may be formed of a biological material, such as a bone graft material, or an osteoconductive or osteoinductive material.

In accordance with certain specific applications, the device 10 has particular utility as a lateral implant for insertion into the intradiscal space using a lateral approach as more fully described in PCT Application No. PCT/US2012/054055, entitled "Lateral Approach Expandable Spinal Implant and Method", filed on Sep. 7, 2012 and commonly assigned to the same assignee as the present invention, the disclosure of which is incorporated herein by reference in its entirety. As such, the overall length L of the device 10 as shown in FIGS. 5-6, including the lengths of both the superior endplate 12 and the inferior endplate 14, is about 37 mm. The width Ws of the superior endplate 12 is approximately 12.5 mm and the width Wi of the inferior endplate 14 is approximately 17.3 mm. The height of the unexpanded device 10 of FIGS. 1-2 with the superior endplate 12 fully nested within the inferior endplate 14 is approximately 8 mm. With the introduction of four wafers 100, each of which has a thickness of approximately 1.0 mm, the height of device 10 may be expanded from an unexpanded height of approximately 8 mm to an expanded height of approximately 12 mm. Of course, the number of wafers may vary depending upon the particular surgery and the initial height may also be different. For example, device 10 may be formed to have an initial unexpanded height of 9 mm and with the addition of five wafers 100, each having a thickness of 1 mm, the height of device 10 may be increased to 14 mm. As such, it should be appreciated that these dimensions are only illustrative and that the dimensions of the device 10 and the number of wafers 100 to be inserted and their thicknesses may vary depending upon the application.

The footprint of the outer surfaces of the superior and inferior endplates 12, 14 that contacts the endplates of opposing vertebral bodies is determined by the area defined by the perimeter of such outer surfaces. Thus the footprint of outer surface 12*a* is L times Ws, as shown in FIG. 5. In the particular example above with device 10 having a 37 mm length, the footprint is approximately 461 $mm^2$. The bone graft area that contacts the endplate of the superior vertebral body is defined by the area of the single opening 62*a*, which in this example is approximately 95 $mm^2$. The ratio of bone graft area to the footprint at outer surface 12*a* is therefore about 20.6%. The footprint of the outer surface 14*a* of the inferior endplate 14 that contacts the endplate of the inferior vertebral body is defined by the area, L times Wi, as shown in FIG. 6. In this particular example, the footprint is approximately 639 $mm^2$. The bone graft area that contacts the endplate of the superior vertebral body is defined by the total area of the two openings together with the countersink areas 36*a*, which in this example is approximately 98 $mm^2$. The ratio of bone graft area to the footprint at outer surface 14*a* is therefore about 15.3%.

Turning now to FIGS. 12-18 a second embodiment of the invention is described. An expandable interbody fusion device 200 comprises a superior endplate 212, an inferior endplate 214 and a plurality of interlocking wafers 300. Components of interbody fusion device 200 are substantially the same both structurally and functionally as like components of interbody fusion device 10, except for several differences. The first difference is that device 200 is of smaller size than device 10 and is particularly shorter in length. The device 200 thus has particular utility as a spinal implant inserted posteriorly or posteriolaterally either bilaterally or unilaterally depending upon the surgical indication and the surgeon's preference.

The second difference of device 200 over device 10 is that the superior endplate 212 is not fully nested within the sidewalls 216, 218 and the front end wall 220 and the rear end wall 222 of device 200. Each side wall 216, 218 defines upper surfaces 216*a* and 218*a* extending lengthwise thereon. Rear end wall 220 defines a recess 220*a* extending therein at that the upper surface thereof and front end wall 222 defines an upper surface 222*a* coplanar with upper surfaces 216*a* and 218*a*. Superior endplate 212 includes a flange 254 projecting outwardly and longitudinally from the hub 240 at the rear proximal end surface 246 and a flange 256 projecting outwardly and longitudinally from the hub 240 at the front distal end surface 248 at the front distal end surface 248. Flanges 257 and 259 project outwardly and laterally from the hub 240 from hub side surfaces 242 and 244, respectively. In the unexpanded condition, the flanges 256, 257 and 259 rest on top of respective upper surfaces 222*a*, 216*a* and 218*a* with a flange 254 residing in recess 220*a*. While not fully nested in a manner as provided with device 10, the added expanse of the flanges 256, 257 and 259 provides for a larger footprint than the fully nested structure.

Figure 15:
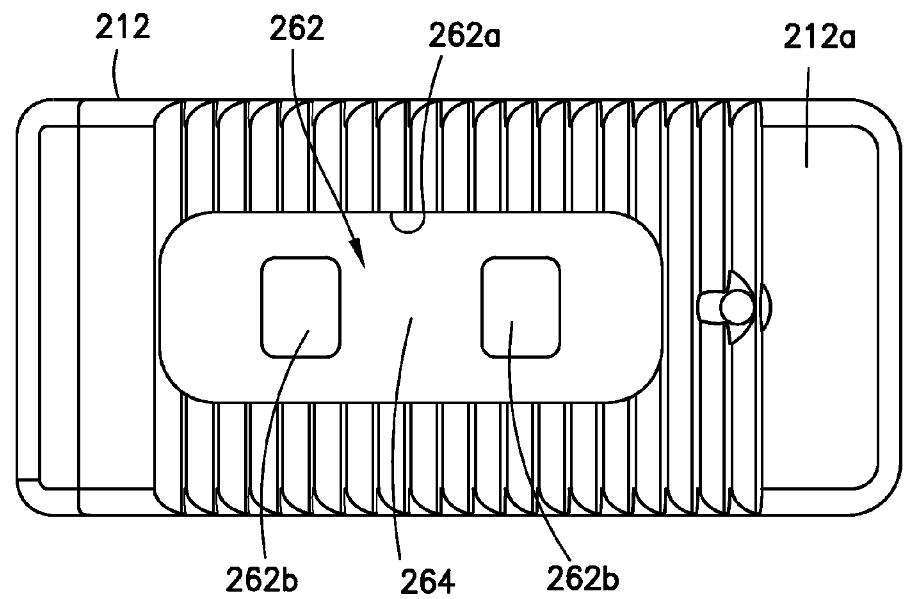
FIG. 15 is a top plan view of the interbody fusion device of FIG. 12.
Figure 16:
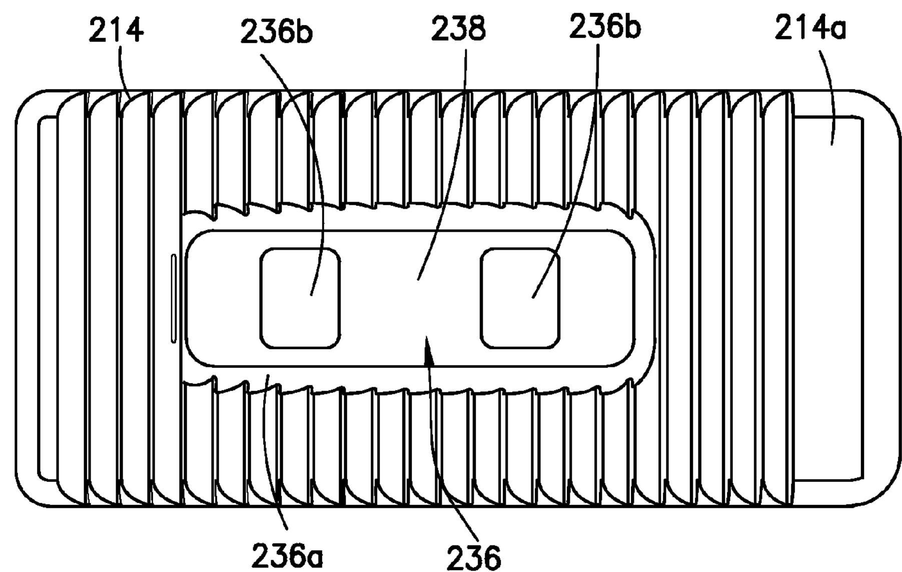
FIG. 16 is a bottom plan view of the interbody fusion device of FIG. 12.
Figure 17:
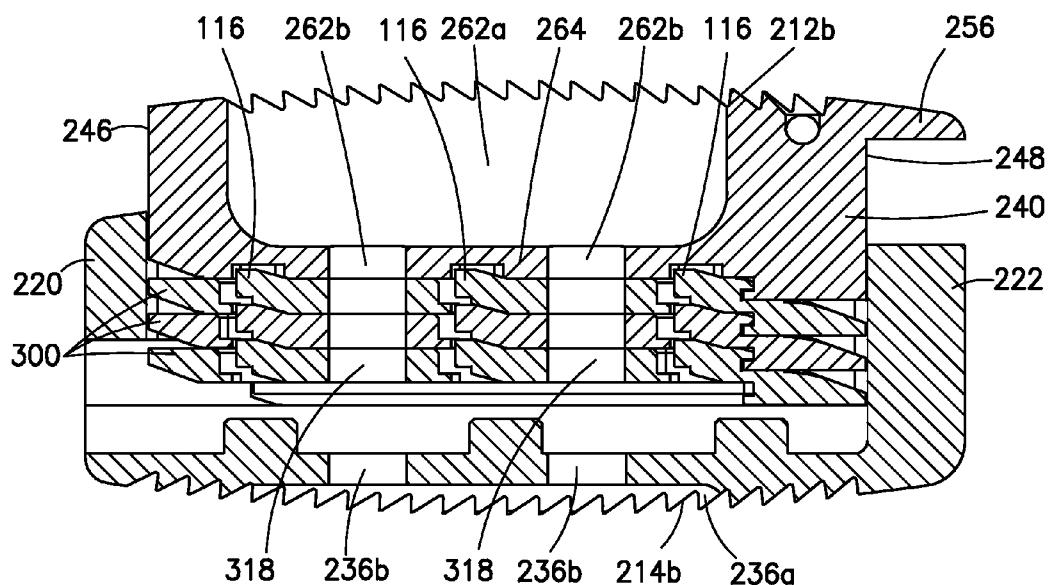
FIG. 17 is a cross section of the expanded interbody fusion device as seen along the viewing lines XVII-XVII of FIG. 14.
Figure 18:
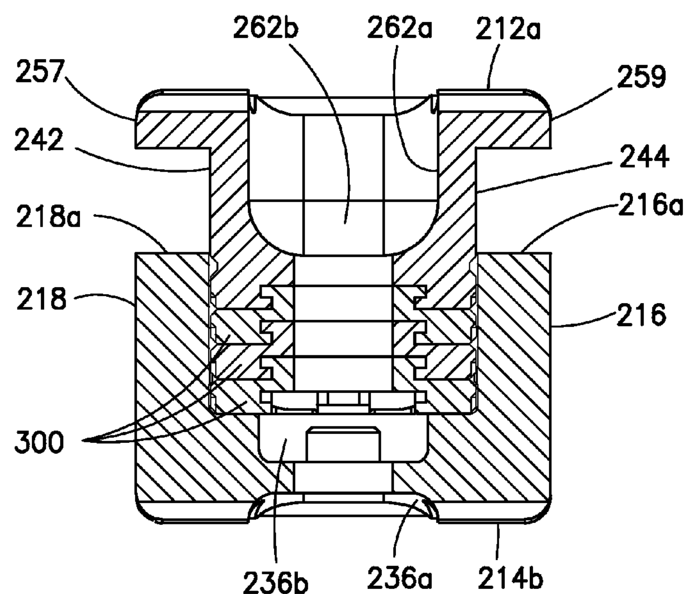
FIG. 18 is a cross section of the expanded interbody fusion device as seen along the viewing lines XVIII-XVIII of FIG. 14.

A third difference of device 200 over device 10 is that device 200 has multi-contoured openings at both the upper surface 212*a* and 214*a*, as shown in FIGS. 15 and 16. The superior endplate 212 has an opening 262 therethrough, the upper portion of opening 262 being a single, oval-shaped opening 262*a*. The lower portion of opening 262 comprises a pair of generally rectangular openings 262*b* separated by a cross member 264 disposed generally centrally and laterally across superior endplate 212. Openings 262*b* extend generally linearly along the longitudinal direction of superior endplate 12. The inferior endplate 214 has an opening 236 therethrough, the lower portion of opening 236 being a single, oval-shaped opening 236*a*. The upper portion of opening 236 comprises a pair of generally rectangular openings 236*b* separated by a cross member 238 disposed generally centrally and laterally across inferior endplate 214. Openings 236*b* extend generally linearly along the longitudinal direction of superior endplate 12 and are disposed therethrough such that in assembly with superior endplate 212 openings 236*b* are generally in alignment in the elongate direction with openings 262*b* through superior endplate 212. It should be appreciated that the area of bone graft contact with the endplates of opposing vertebral bodies may be maximized by the use of the multi-contoured openings 236 and 262 each of which has a substantially large single oval-shaped opening 236*a* and 262*a*, respectively, while maintaining strength of the endplates 212, 214 due to the cross members 238 and 264.

A fourth difference of device 200 over device 10 is that the ribs 212*b* and 214*b* are configured to include a saw tooth shape rather than the pyramidal configuration of the ribs 12*b* and 14*b* of the device 10.

The expansion members defined by interlocking wafers 300 are substantially similar to wafers 100 except for size and are inserted in a similar manner such that once inserted the holes 318 are aligned and in communication with openings 236*b* through the inferior endplate 214 and with openings 262*b* through the superior endplate 212.

Figure 12:
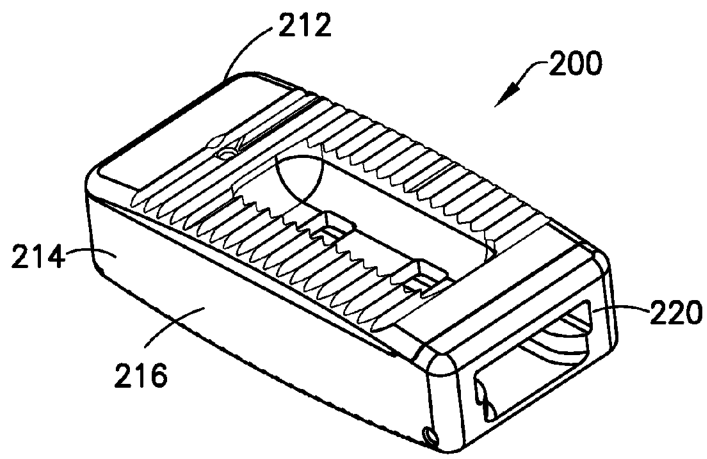
FIGS. 12 and 13 are rear and front perspective views respectively of an expandable interbody fusion device in unexpanded condition in accordance with another embodiment of the present invention.
Figure 13:
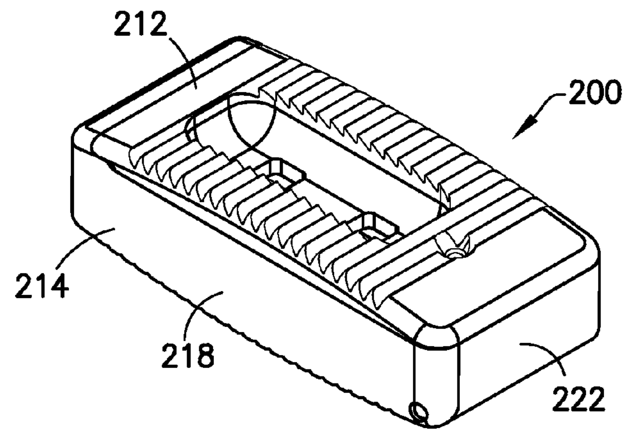
Figure 14:
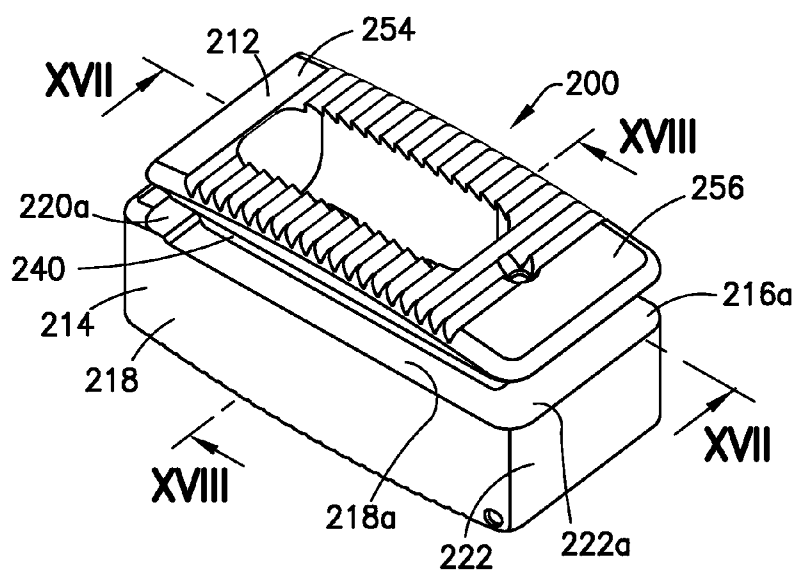
FIG. 14 is a front perspective view of the expandable interbody fusion device of FIG. 13 in expanded condition.

In an example of the second embodiment, the overall length L of the device 200 is about 25 mm and the overall width is approximately 12 mm. The height of the unexpanded device 10 of FIGS. 12-13 is approximately 7 mm. With the introduction of each wafer 300 having a thickness of approximately 1.0 mm, the height of device 200 may be expanded in 1 mm increments. As such, the insertion of one wafer 300 would increase the height of device 200 to 8 mm while the addition of three wafers 300 would increase the height to 10 mm. As with device 10, it is preferable that all the wafers 300, but at least the two lowermost wafers 300 where more than a single wafer is inserted, be contained within and constricted by the opposing side walls 216, 218 and the rear and front end walls 220, 222 so as to provide additional resistance against torsional movement of the spine. It should be appreciated that with this embodiment other unexpanded starting heights and lengths of device 200 may be contemplated as well as different number of wafers 300 and wafer thicknesses, depending upon the particular application. For example, a device having an overall length of approximately 29 mm and a width of approximately 12 mm may have an unexpanded height of about 9 mm with three wafers 300 inserted to thereby increase the height to about 12 mm.

In the particular example above with device 200 having a 25 mm length, the footprint of outer surface 212*a* of superior endplate 212 is approximately 283 $mm^2$. The bone graft area that contacts the endplate of the superior vertebral body is defined by the area of the single opening 262*a*, which in this example is approximately 78 $mm^2$. The ratio of bone graft area to the footprint at outer surface 212*a* is therefore about 27.6%. The footprint of the outer surface 214*a* of the inferior endplate 214 that contacts the endplate of the inferior vertebral body in this particular example is approximately 305 $mm^2$. The bone graft area that contacts the endplate of the inferior vertebral body is defined by the area of the single opening 236*a*, which in this example is approximately 78 $mm^2$. The ratio of bone graft area to the footprint at outer surface 214*a* is therefore about 25.6%. Accordingly, the ratio of bone graft area to the footprint at the outer surfaces of the expandable interbody fusion devices in the examples ranges from about 15 to 28%.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, the superior and inferior endplates of the expandable interbody fusion device may each have a single opening extending therethrough in communication and alignment with at least one expansion members defined by an interlocking wafer. Such wafer would have at least two locking elements thereon, one locking element being located on each side of the hole through such wafer, such that a locking engagement would be provided at each of the proximal and distal ends of the device. Also, while the illustrated embodiments have been directed to interbody fusion of the spine, the expandable devices and wafers disclosed herein may be used in other applications that require distraction of tissue surfaces. Modifications in size may be necessary depending upon the body space being distracted.

What is claimed is:

1. An expandable interbody fusion device for implantation into an intradiscal space between two opposing vertebral bodies of a spine, comprising:

a first elongate endplate having an outer surface configured to contact one of said vertebral bodies and a hub having a mating surface opposite to said outer surface of said first endplate, said first endplate having side surfaces extending downwardly from said outer surface, said side surfaces extending along opposite sides of said hub, said hub having spaced-apart first and second end surfaces extending between said side surfaces, said mating surface including a mating feature thereon, said first endplate having at least one opening extending through said outer surface and said mating surface, said first endplate defining a flange having a portion projecting outwardly from said hub at one of the first end surface and the second end surface in the elongate direction;

a second elongate endplate having an outer surface configured to contact the other vertebral body, said second endplate having opposing spaced apart side walls, opposite spaced end walls and a support surface between said opposite side walls and said opposite end walls and opposite to said outer surface of said second end plate, said opposite side walls, said opposite end walls and said support surface defining a cavity, said hub of said first endplate being received within said cavity and facing said support surface, said side surfaces of said hub being received within said side walls of said second endplate, said second endplate having at least one opening extending through said outer surface and said support surface and communicating with said cavity, said opposite side walls of said second endplate each terminating in an upper surface extending generally parallel to each other along the elongate direction, said opposite end walls of said second endplate each terminating in an upper surface with a recess extending into at least one of said upper surfaces of said end walls between said side walls, the outer surface of said first endplate being substantially flush with the upper surfaces of said side walls and said flange of said first endplate residing in said recess when the device is unexpanded; and an elongate expansion member sized to be received into said cavity and supported on said support surface, and upon receipt therein to move said first endplate and said second endplate relatively apart, said elongate expansion member having opposing upper and lower surfaces, said elongate expansion member having a hole extending through said upper and lower surfaces and a complementary mating interface for interlocking engagement with said mating feature on said mating surface, said complementary mating interface, projecting from at least one of said upper surface and said lower surface, including at least two locking elements, said hole being located between two of said locking elements, said hole being located such that upon receipt of said elongate expansion member into said cavity said hole communicates with said openings through said first endplate and said second endplate.

2. The device of claim 1, wherein said device includes a releasable engagement feature between said first endplate and said second endplate defined by a rib on each interior side wall of said second endplate and a groove on opposite sides of the hub of said first endplate.

3. An expandable interbody fusion device for implantation into an intradiscal space between two opposing vertebral bodies of a spine, comprising:

a first elongate endplate having side surfaces, an outer surface configured to contact one of said vertebral bodies and a lower surface opposite to said first endplate outer surface and having a shaped configuration, said first endplate defining an outer perimeter and having a multi-contoured opening disposed fully within said perimeter and extending through said outer surface and said lower surface, said multi-contoured opening having a single opening through the outer surface of said first endplate and at least two openings through the lower surface of said first endplate and communicating with said single opening through the outer surface of said first end plate, said two openings at the lower surface of said first endplate being spaced apart from one another by a cross member extending transversely across the first endplate at the lower surface thereof and comprising at least a portion of said shaped configuration;

a second elongate endplate having an outer surface configured to contact the other vertebral body and an upper support surface opposite said second endplate outer surface, said second endplate having opposing spaced apart side walls projecting upwardly from said upper support surface toward said first endplate, said second endplate and said first endplate being initially disposed in a first position such that said lower surface of said first endplate and said upper support surface of said second endplate generally face each other with said side surfaces of said first endplate being at least partially received within said side walls of said second endplate, said second endplate having at least one opening extending through said outer surface and through said upper support surface; and at least one elongate expansion member sized to be received into said device and supported on said upper support surface between said first endplate and said second endplate, and upon receipt therein to move said first endplate and said second endplate relatively apart, said elongate expansion member having opposing upper and lower surfaces, said expansion member having at least one hole extending through said upper and lower surfaces and including a mating feature projecting from at least one of said upper surface and said lower surface, said mating feature including at least two locking elements, one locking element being disposed on each side of said at least one hole along said elongate direction;

said expansion member forming upon receipt into said device an interlocking interface between said mating feature and the shaped configuration of the lower surface of said first endplate wherein one of said two locking elements engages the shaped configuration of the lower surface of said first endplate at said cross member, said at least one hole being located such that upon receipt of said elongate expansion member into said device said at least one hole communicates with said multi-contoured opening through said first endplate and said at least one opening through said second endplate.

4. The device of claim 3, wherein said two openings at said lower surface extend along the elongate direction of said first endplate.

5. The device of claim 3, wherein said at least two locking elements includes three locking elements and said at least one hole includes two holes located generally linearly along the elongate direction, one locking element being disposed adjacent each end of the expansion member and one locking element being disposed generally centrally with one hole being disposed on each side of the generally centrally disposed locking element, said two holes being located such that upon receipt of said elongate expansion member into said device said holes communicate with said two openings at the lower surface of said first endplate.

6. The device of claim 5, wherein said at least one opening includes at least two openings extending through said outer surface and said upper support surface extending along the elongate direction, two of said openings being located such that upon receipt of said elongate expansion member into said device said two openings communicate with said two holes through said expansion member.

7. The device of claim 6, wherein each of said locking elements comprises a resiliently deflectable locking surface.

8. The device of claim 3, wherein said first position of said first endplate and said second endplate is defined by a releasable engagement between said first endplate and said sidewalls.

9. The device of claim 8, wherein said expansion member is defined by a generally elongate flat wafer having side edges for said upper and opposing lower surfaces.

10. The device of claim 9, wherein said device comprises at least one further wafer received between said wafer and said upper support surface of said second endplate, said further wafer defining a resilient interlocking interface with said wafer, said wafer and said further wafer being contained within the sidewalls of said second endplate.

11. The device of claim 3, wherein said at least one opening extending through said outer surface and said upper support surface of said second endplate is a multi-contoured opening.

12. The device of claim 11, wherein said multi-contoured opening through said second endplate has a single opening through the outer surface of said second endplate and at least two openings through the upper support surface of said second endplate communicating with said single opening.

13. The device of claim 12, wherein said two openings at the upper support surface of said second endplate are spaced by a cross member extending transversely across the second endplate at the upper surface thereof.

14. The device of claim 13, wherein the perimeter of the outer surfaces of each of said first endplate and said second endplate defines a respective footprint, and wherein each of the at least one opening of said first endplate and said second endplate defines a bone graft area for contacting opposing vertebral bodies.

15. The device of claim 14, wherein the ratio of the bone graft area to the footprint of at least one of said first endplate and said second endplate ranges from about 15 to 28%.

* * * * *